United States Patent
Cesbron et al.

(12) 
(10) Patent No.: US 6,392,014 B1
(45) Date of Patent: *May 21, 2002

(54) **CLONING OF GENE ENCODING THE GP28.5 PROTEIN OF *TOXOPLASMA GONDII*; PEPTIDE FRAGMENTS OF SAID PROTEIN AND THEIR APPLICATIONS**

(76) Inventors: Marie-France Cesbron, 2, Avenue Barrois, 59700 Marcq-en-Baroeul; Corinne Mercier, 49, rue Croix de Glageon, 59177 Sains du Nord; André Capron, 58, rue du Capitaine Jasmin, 59133 Phalempin; André Tartar, Rue du Moulin, 62490 Vitry en Artois; Pierrette Maes, 11, Avenue du Roi Albert ler, 59290 Wasquehal, all of (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/092,179

(22) Filed: Jun. 5, 1998

Related U.S. Application Data

(62) Division of application No. 08/338,543, filed as application No. PCT/FR93/00575 on Jun. 15, 1993, now Pat. No. 5,824,788.

(30) Foreign Application Priority Data

Jun. 15, 1992 (FR) .............................. 92 07206

(51) Int. Cl.[7] .................. C07K 1/00; C07K 17/00; A61K 38/00; A61K 39/002; A61K 39/012
(52) U.S. Cl. .................. 530/350; 530/300; 530/324; 530/325; 530/326; 530/327; 530/328; 530/329; 530/330; 530/387.1; 530/388.1; 530/388.6; 530/387.9; 424/184.1; 424/185.1; 424/191.1; 424/192.1; 424/265.1; 424/269.1; 424/273.1; 424/278.1
(58) Field of Search ................. 530/350, 300, 530/324, 325–329, 330, 387.9, 387.1, 388.1, 388.6; 424/184.1, 191.1, 192.1, 185.1, 278.1, 265.1, 269.1, 273.1

(56) References Cited

U.S. PATENT DOCUMENTS

| 5,633,139 A | 5/1997 | Prince et al. |
| 5,665,542 A | 9/1997 | Prince et al. |
| 5,686,575 A | 11/1997 | Prince et al. |
| 5,824,788 A | * 10/1998 | Cesbron et al. |
| 5,859,196 A | * 1/1999 | Boothroyd et al. |
| 6,022,546 A | * 2/2000 | Knapp et al. |

OTHER PUBLICATIONS

Cesbron–Delauw et al. Research in Immunol (Immunobiolof Toxoplasmosis) 144/1:41–44, 1993.*
Torpier et al. Exptal. Parasitology, 77:13–22, 1993.*
Parmley et al. Mol & Biochem. Parasitology 57:161–165, 1993.*
Mercier et al. Mol. & Biochem. Parantology 58:71–82, 1993.*
Cesbron–Delauw et al. Mal. Immunology 29/11: 1375–1382, 1992.*
Prince et al., Mol & Biochem. Parasitology 34:3–14, 1989.*
Godard et al., Infection & Immunity 58/8: 2446–2451, Aug. 1990.*
Charif et al, Exptal. Parasitology, 71:114–124, 1990.*
Ferguson et al. Parasite Immunology 10: 465–479. 1988.*
Darcy et al. Parasitol. Res. 76: 473–478, 1990.*
L.D. Sibley et al, "Ultrastructural localization of an intracellular Toxoplasma protein that induces protectionin mice", Infection and Immunity, vol. 55, No. 9., pp. 2137–2141, Sep. 1987.
M.A. Leriche et al, "Characterization of the protein contents of rhoptries and dense granules of *Toxoplasma gondii* tachyzoites by subcellular fractionation and monoclonal antibodies", Molecular and Biochemical Parasitology, vol. 45, pp. 249–260, 1991.
A. Achbarou et al, "Differential targeting of dense granule proteins in the parasitophorous vacuole of *Toxoplasma gondii*", Parasitology, vol. 103, No. 3., pp. 321–329, 1991.
A. Murray et al, "Multiple B–cell eptopes in a recombinant GRA2 secreted antigen of *Toxoplasma gondii*", Applied Parasitology, vol. 34, No. 4., pp. 235–244, 1993 (Abstract only).
Monday, Minisymposium 4: Cell Biology of Parasitic Protozoa (22–25), J. Cell Biol., vol. 115 3 parts, 1991.
Prince et al, "Cloning of cDNAs encoding a 28 kilodalton antigen of *Toxoplasma gondii*", Molecular and Biochemical Parasitology, vol. 34, pp. 3–14, 1989.
Murray et al, "Multiple B–cell epitopes in a recombinant GRA2 secreted antigen of *Toxoplasma gondii*", Applied Parasitology, vol. 34, pp. 235–244, 1993.
Cesbron–DeLauw et al, "Amino acid sequence requirements for the epitope recognized by a monoclonal antibody reacting with the secreted antigen GP28.5 of *Toxoplasma gondii*", Molecular Immunology, vol. 29, No. 11, pp. 1375–1382, 1992.

* cited by examiner

*Primary Examiner*—N M Minifield
(74) *Attorney, Agent, or Firm*—Oblon, Spivak, McClelland, Maier & Neustadt, P.C.

(57) ABSTRACT

The invention relates to cloning of the gene for the toxoplasma GP28.5 antigen. It also encompasses purified GP28.5 antigen preparations and antigenic polypeptides derived from said antigen, and their applications.

12 Claims, 3 Drawing Sheets

CLONING OF GENE ENCODING THE GP28.5 PROTEIN OF *TOXOPLASMA GONDII*; PEPTIDE FRAGMENTS OF SAID PROTEIN AND THEIR APPLICATIONS

This application is a Divisional of U.S. application Ser. No. 08/338,543, filed on Jan. 30, 1995, now U.S. Pat. No. 5,824,788, which was filed as International Application Ser. No. PCT/FR93/00575, filed Jun. 15, 1993.

The present invention relates to the cloning of the gene encoding a 28.5 kDa Toxoplasma excretion-secretion antigen, and to the production of peptide fragments representing epitopes thereof, as well as to preparations of said antigen and of its fragments, and to their uses.

Toxoplasmosis is one of the most widespread protozoal infections, both in man and in animals. It is responsible for about 25% of deaths in AIDS patients. The congenital infection, the cause of abortions or severe neonatal malformations in man and domestic animals, could be prevented. Indeed, it is known that the primary infection induces a long-lasting immunity.

In the search for protective antigens permitting the development of a vaccine against toxoplasmosis, various antigens have been studied. The inventors' team was in particular interested in the excretion-secretion antigens (ESA) of the tachyzoites. It has indeed been established, during experiments both in man and in animals, that the ESA antigens were immunogenic. It was also shown that some ESAs possess epitopes in common with antigens of bradyzoites. However, bradyzoites are the resistant form of the parasite.

Various approaches, comprising in particular the production of monoclonal antibodies, colloidal gold labeling, and molecular biology, led the inventors' team to the characterization of four common antigens [CHARIF et al. Exp. Parasitol., 71:117 (1990)], [CESBRON-DELAUW et al., Proc. Natl. Acad. Sci. USA, 86:7537 (1989)], [DARCY et al., Parasitol. Res. 76:478, (1990)]. The main one, called Gra2 or GP28.5, is a glycoprotein of 28.5 kDa, and it has been shown that it is a constituent of the matrix of the dense granules of tachyzoites, and that it is associated with the microvilli network of the parasitophorus vacuole of the parasite, after invasion of the host.

A 28 kDa antigen (P28), considered as being similar to the GP28.5 antigen, has been described by SIBLEY and SHARMA [SIBLEY et al. Infect. Immun. 55:2137 (1987)], and a DNA sequence encoding this antigen has been published by PRINCE et al. [Molec. Biochem. Parasitol. 34:3 (1989)].

SUMMARY OF THE INVENTION

The present invention set itself the aim of producing purified preparations of the GP28.5 antigen, as well as of producing this antigen in recombinant form, and its immunological characterization. In particular, the aim of the present invention is the localization and the characterization of specific epitopes of the GP28.5 antigen.

The inventors succeeded in obtaining a purified preparation of the GP28.5 antigen, and demonstrated the protective effect of an immunization by this preparation against *Toxoplasma gondii* infection in mice.

The inventors also cloned the entire gene encoding the GP28.5 antigen, and located the introns and exons, as well as the 5' and 3' noncoding regions.

DETAILED DESCRIPTION OF THE INVENTION

The subject of the present invention is a nucleic acid fragment, which comprises a sequence encoding the Toxoplasma GP28.5 antigen. A nucleic acid fragment conforming to the invention is represented in the list of sequences in the annex under the number SEQ.ID.NO:1. "Sequence encoding the Toxoplasma GP28.5 antigen" is understood to mean not only the coding sequence identified in the sequence SEQ.ID.NO:1, but also any sequence which, taking into account the degeneracy of the genetic code, encodes the polypeptide represented in the list of sequences in the annex under the number SEQ.ID.NO:2.

The inventors also showed that the GP28.5 antigen contains several major epitopes specific for the B cells; one of them, which is recognized by a mouse monoclonal antibody called TG17-179 [CHARIF et al., Exp. Parasitol., 71:117 (1990)] is located at the C-terminal end of the molecule.

The inventors characterized this epitope and showed that it contained at least the 5 C-terminal amino acids of GP28.5. In addition, they showed that this epitope is also a major epitope recognized by human polyclonal antibodies directed against *T. gondii*.

The invention also encompasses nucleic acid fragments which encode polypeptides representing epitopes of the GP28.5 antigen.

According to a preferred embodiment of the present invention, said nucleic acid fragment encodes a polypeptide comprising at least the 5 C-terminal amino acids of the sequence SEQ.ID.NO:2.

According to another preferred embodiment of the invention, said nucleic acid fragment encodes a polypeptide comprising fragment 24–129 of the sequence SEQ.ID.NO:2.

According to yet another preferred embodiment of the invention, said nucleic acid fragment encodes a polypeptide comprising fragment 127–176 of the sequence SEQ.ID.NO:2.

The subject of the invention is also recombinant vectors (plasmids, viruses and the like), which comprise at least one nucleic acid fragment as defined above, encoding the Toxoplasma GP28.5 antigen, or a peptide fragment representing an epitope thereof.

Said vectors are in particular expression vectors, comprising sequences of the promoter type, terminator type and the like.

The subject of the present invention is also transformed eukaryotic or prokaryotic cells (and in particular microorganisms), which contain at least one recombinant vector in accordance with the invention.

The subject of the invention is also a polypeptide of 185 amino acids whose sequence which is represented in the list of sequences in the annex under the number SEQ.ID.NO:2, is that of the Toxoplasma GP28.5 antigen.

The invention also encompasses the polypeptides whose sequence differs from the abovementioned sequence only by a few amino acids, in particular polypeptides representing allelic variants or isoforms of the GP28.5 antigen.

The invention also comprises recombinant proteins comprising all or part of the sequence of the SEQ.ID.NO:2 sequence, optionally fused with another polypeptide sequence; within this framework, the subject of the invention is in particular:

a recombinant protein of 212 amino acids, comprising the entire sequence of the GP28.5 antigen;

a recombinant protein comprising amino acids 127–176 of the sequence SEQ.ID.NO:2;

a recombinant protein comprising amino acids 1–129 of the sequence SEQ.ID.NO:2;

a recombinant protein comprising amino acids 24–129 of the sequence SEQ.ID.NO:2.

The invention also relates to a process for producing a recombinant protein as defined above, which process comprises a step during which the transformed cells as defined above, comprising at least one DNA fragment in accordance with the invention, are cultured.

The recombinant polypeptides in accordance with the invention, when expressed in E. coli, conserve major epitopes involved in the polyclonal response to the GP28.5 antigen, and do so even though the expression in E. coli does not maintain the structural integrity of the GP28.5 protein which is a glycosylated protein.

If it is desired, however, to obtain other epitopes such as epitopes of carbohydrate nature, or epitopes corresponding to tertiary and quaternary structures, it will be chosen to produce the recombinant GP28.5 in eukaryotic systems such as for example yeasts or baculoviruses.

The inventors, in addition, showed that the C-terminal sequence of fifteen amino acids of the GP28.5 antigen represents an epitope recognized by a number of sera from patients suffering from acute or chronic infections, and also located other major B epitopes in the fragment corresponding to amino acids 127–176 of the sequence SEQ.ID.NO:2. In addition, the inventors located other regions between amino acids 24 and 129, and in particular the regions corresponding to amino acids 55–70 and to amino acids 140–160 of the sequence SEQ.ID.NO:2, which comprise epitopes of the GP28.5 antigen which are recognized by the human sera.

The subject of the invention is also peptides comprising at least one epitope of the GP28.5 antigen.

According to a preferred embodiment of the invention, the said peptide comprises the 5 C-terminal amino acids of the sequence SEQ.ID.NO:2.

According to a preferred arrangement of this embodiment, the said peptide comprises between 5 and 15 C-terminal amino acids of the sequence SEQ.ID.NO:2.

According to a preferred feature of this arrangement, said peptide comprises the 8 C-terminal amino acids of the sequence SEQ.ID.NO:2.

According to another preferred embodiment of the invention, said peptide comprises amino acids 24–129 of the sequence SEQ.ID.NO:2.

According to another preferred embodiment of the invention, said peptide comprises amino acids 55 to 70 of the sequence SEQ.ID.NO:2.

According to yet another preferred embodiment of the invention, said peptide comprises amino acids 140 to 160 of the sequence SEQ.ID.NO:2.

The sequence of the 5 C-terminal amino acids of the GP28.5 antigen is recognized in immunotransfer by the mouse monoclonal antibody TG 17-179. A competitive ELISA with longer peptides has shown that the immunoreactivity was conserved for peptides of 8 residues or more, and lost when the peptide was reduced to the last 6 C-terminal residues or less. Experiments with the octapeptide lacking the C-terminal glutamine residue showed that it was then 20 times less active. On the other hand, neither the addition of residues to the C-terminal end, nor the substitution of the terminal COOH functional group change the immunoreactivity of the epitope. In addition, competition experiments between the monoclonal antibody TG 17-179 and sera from infected patients showed that the epitope defined by this monoclonal antibody is also a major epitope for the human polyclonal antibodies.

The subject of the invention is also antigenic compositions which comprise at least one antigen chosen from the group consisting of:

a purified preparation of GP28.5 antigen;

a polypeptide of sequence SEQ.ID.NO:2;

a fragment of said polypeptide representing an epitope of the GP28.5 antigen;

a recombinant protein comprising all or part of the sequence SEQ.ID.NO:2.

The invention also encompasses a process for preparing polyclonal or monoclonal anti-GP28.5 antibodies which comprises a step during which an animal is immunized with an antigenic composition in accordance with the invention.

The antigenic compositions in accordance with the invention also permit the preparation of diagnostic reagents or anti-Toxoplasma vaccines. The invention also encompasses these reagents and these vaccines.

The present invention will be understood more clearly with the aid of the additional description below, which refers to examples relating to the cloning of the gene encoding the GP28.5 antigen of *Toxoplasma gondii*, and the identification of the specific epitopes of this antigen.

I) CLONING AND EXPRESSION OF THE GENE ENCODING GP28.5 OF T. GONDII

Figure 1:
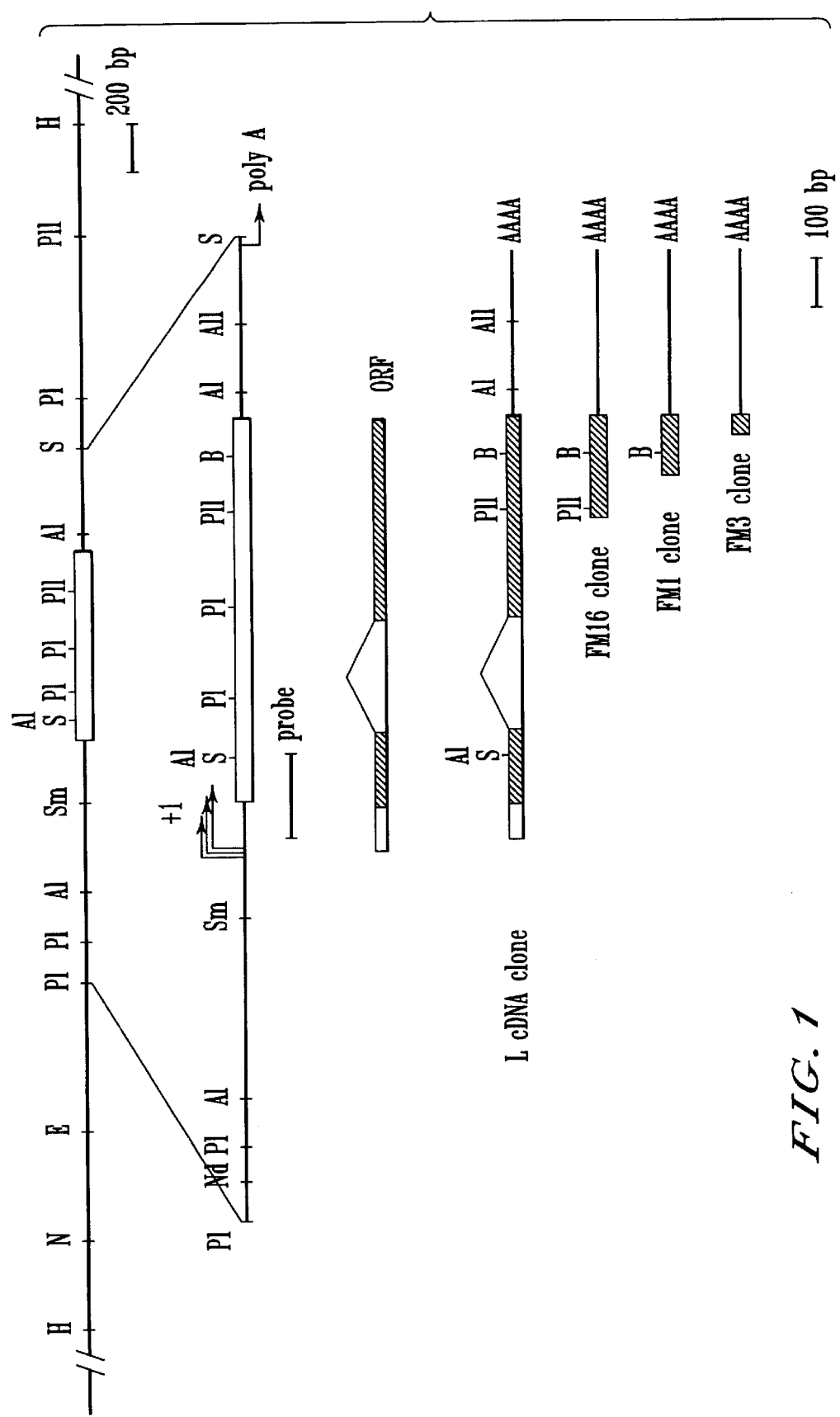
FIG. 1: The partial restriction map on 5 kb of the genomic clone Gra2-EMBL3, and the partial restriction map of a 2040 bp region thereof. The FIG. also shows the transcribed region and the region encoding the GP28.5 protein. The rest of the FIGURE is a magnification of a 2040 bp region which represents a subclone of the GP28.5 genomic clone, and contains the gene encoding GP28.5 and the flanking sequences of 78 bp in the 5' and 32 bp in the 3'. The open reading frame is indicated. The E coRI-SalI fragment of 195 base pairs that was used as a probe for screening the libraries is indicated under the restriction maps and the cDNA clones: LcDNA, FM 16, FMI, and FM3. The sequence AAAA indicates the poly A tail of the transcripts. The coding regions are shaded. The restriction sites are indicated by the following abbreviations: AI=AccI, AII=AvaII, B=BglI, E=EcoRV, H=HindIII, N=NaeI, ND=NdeI, PI=PstI, PII=PvuII, S=SalI, SM=SmaI.

Unless otherwise stated, the techniques for the manipulation of nucleic acids and of molecular cloning which are used in the examples below are those described by SAMBROOK et al. [A Laboratory Manual (second edition), Cold Spring Harbor Laboratory Press, Cold Spring Harbor, N.Y. (1989)].

The TG17-179 antibody was obtained from BALB/C mice immunized with ESAs antigens as described by CHARIF et al. [Exp. Parasitol. 71:114 (1990)].

EXAMPLE 1

Cloning of the Gene Encoding GP28.5 OF T. Gondii

1) Production of the Toxoplasmas.

Tachyzoites were obtained from the peritoneal fluid of mice infected three days earlier with the strain RH of

*Toxoplasma gondii*. The parasites were harvested in RPMI 1640 medium (GIBCO BRL), filtered through polycarbonate membranes (pore diameter 3 microns) (NUCLEPORE) and washed twice in the same medium.

2) Preparation of *Toxoplasma gondii* nucleic acid. Total RNA was isolated from tachyzoites of *Toxoplasma gondii* strain RH by extraction with lithium/urea, and the poly(A+) RNA was purified by passing through an oligo(dT)-cellulose column.

3) Construction of the tachyzoites cDNA library.

a) Construction in λgt11

The construction of the Toxoplasma cDNA library in the lambda gt11 phage has been described by CESBRON-DELAUW et al. [CESBRON-DELAUW et al. Proc. Natl. acad. Sci. USA, 86:7537 (1989)]. The library, after amplification, was plated on *E. coli* Y1090 cells and screened using the monoclonal antibody TG17-179. The positive clones were detected by incubation with peroxidase-conjugated anti-mouse IgG antibodies, followed by labeling with 4-chloro-1-naphthol.

Three λgt11 clones were selected: they are clones FM3, FM1 and FM16, containing respectively inserts of 450, 550 and 650 base pairs. EcoRI restriction fragments of these clones were subcloned into the vectors M13, mp18 and mp19, and sequenced by the SANGER method [FEINBERG et al. Anal. Biochem. 137:266 (1984)].

The sequencing showed that these three clones all encode the C-terminal end of GP28.5.

b) Construction in λZapII

The tachyzoite cDNA library was constructed in the λZapII vector using "ZAP cDNA SYNTHESIS KIT" (STRATAGENE). The cDNA was synthesized using, as template, 5 μg of polyA RNA from the tachyzoites, with the aid of reverse transcriptase (MMLVRT) for the synthesis of the first strand, and DNA polymerase I and RNase H for the synthesis of the second strand. After ligation in 3' of an EcoRI adaptor, and after digestion in 5' with XhoI, the excess adaptor was removed by chromatography on acrylamide-agarose (Ac-A 34, IBF). The cDNAs were then ligated into the LacZ gene of lZapII ("UNI ZAP XR", STRATAGENE) and encapsulated in vitro ("GIGAPAC II GOLD PACKAGING EXTRACT", STRATAGENE). Before amplification, the library comprises $10^6$ recombinant phages.

After amplification, the phages were plated on *E. coli* XLI-Blue and the library was screened with, on the one hand, the mouse polyclonal serum directed against the purified GP28.5 antigen (1/100 dilution) and, on the other hand, the monoclonal antibody TG17-179 (1/500 dilution), both diluted in TBS buffer (10 mM TRIS HCl pH 8, 15 mM NaCl). The coinfection of the bacteria with λZapII and a helper phage (R408, Stratagene) made it possible to excise the phagemide pBluescript containing the cloned cDNA inserts. The single-stranded DNA obtained from the phagemide in the presence of the same helper phage was directly used to sequence the cDNA inserts by the dideoxynucleotide method.

The screening of the cDNA library constructed in the λZapII expression vector allowed the production of longer cDNAs. The longest of them, called "LcDNA" comprises 1100 bp; its sequence in 3' is homologous to that of the P28 of PRINCE et al., but shorter by at least 121 bp in 5'.

4) Construction of a *Toxoplasma gondii* Genomic Library in the Phage EMBL 3:

After partial digestion of the tachyzoite genomic DNA with MboI, the genomic library was constructed as described by CESBRON-DELAUW et al. [Proc. Natl. Acad. Sci., USA, 86:7537 (1989)].

The library constructed in the phage EMBL3 was plated on *E. coli* P2392, and screened with the aid of a restriction fragment of the cDNA (EcoRI-SalI fragment of 195 bp), used as probe, after prior labeling with 32p. The hybridations were carried out at 65° C., in 5×DENHARDT buffer [50×DENHARDT buffer contains 1% BSA, 1% PVP, 1% Ficoll (w/v)] and 6.6×SSC buffer (10×SSC contains 3M NaCl, 0.3M $Na_3C_6H_5O_7.2H_2O$, pH 7.2).

A genomic clone called Gra2-EMBL3 was selected; from this clone, a 2040 bp fragment, comprising the entire gene as well as 780 bp of 5' flanking sequence and 32 bp of 3' flanking sequence, was subcloned.

FIG. 1 represents the partial restriction map on 5 kb of the genomic clone Gra2-EMBL3, as well as the partial restriction map of a 2040 bp region thereof, which comprises the entire GP28.5 gene. This figure also shows the transcribed region and the region encoding the GP28.5 protein.

Southern blot analysis of tachyzoite genomic DNA hybridized with a 1100 bp cDNA probe (clone LcDNA) confirms this restriction map. It also indicates that the gene encoding GP28.5 is probably not repeated in the genome of Toxoplasmas.

The top line is a partial restriction map of the genomic clone Gra2-EMBL3 containing the GP28.5 gene (this gene is indicated by a box). The rest of the figure is a magnification of a 2040 bp region which represents a subclone of the GP28.5 genomic clone, and which contains the gene encoding GP28.5 as well as the flanking sequences of 780 bp in 5' and 32 bp in 3'. The open reading frame of GP28.5 is indicated. The EcoRI-SalI fragment of 195 base pairs which was used as probe for screening the libraries is indicated under the restriction maps as well as the cDNA clones: LcDNA, FM16, FMI, FM3. The sequence AAAA indicates the polyA tail of the transcripts. The coding regions are shaded. The restriction sites are indicated by the following abbreviations: AI=AccI, AII=AvaII; B=BglI; E=EcoRV; H=HindIII; N=NaeI; ND=NdeI; PI=PstI; PII=PvuII; S=SalI; SM=SmaI.

The complete sequence of the GP28.5 gene and of the noncoding 5' and 3' regions is shown in the sequence list in the annex under the number SEQ.ID.NO:1. In order to determine the organization of the GP28.5 gene, the sequence of the genomic library was compared with the sequence of the LcDNA clone.

This comparison shows that the GP28.5 gene consists of two exons (5' exon:251 bp; 3' exon:800 bp) separated by a 239 bp intron.

An initiator ATG codon for translation is present in position 886, and the open reading frame ends at position 1682 with a TAA codon. This open reading frame potentially encodes a protein of 185 amino acids whose theoretical molecular weight is 19.8 kDa. A potential site of cleavage of a signal sequence is situated between alanines 23 and 24. The open reading frame is bordered in 3' by a noncoding sequence of 32 bp. A Northern transfer performed on tachyzoite total RNA reveals a single population of mRNA encoding the GP28.5 protein. The size of the messenger is estimated at approximately 1100 bp, which corresponds to the size of the LcDNA clone.

In order to define more precisely the site of initiation of transcription, a primer extension was carried out with tachyzoite total RNA, using as primer an oligonucleotide (CM10), corresponding to positions 888 to 867 of the sequence. By this method, three different potential sites of initiation of transcription were located, respectively at 105, 103 and 102 bp upstream of the signal for initiation of the translation. The first two may correspond to minor sites of transcription whereas the third is undoubtedly the major site of initiation of transcription.

The amino acid sequence of GP28.5 is 67 amino acids shorter at its N-terminal end than the presumed sequence of the P28 antigen previously published by PRINCE et al. In order to verify the fact that the sequence SEQ.ID.NO:1 is indeed that which encodes the GP28.5 antigen, the corresponding amino acid sequence was compared to that of five peptides resulting from the trypsin cleavage of the GP28.5 antigen purified by HPLC as described below. The sequence of these five peptides was completely found again in the amino acid sequence deduced from that of the open reading frame of the cloned gene.

EXAMPLE 2

Preparation of Recombinant Proteins Comprising Fragments of the GP28.5 Sequence:

1) Fusion proteins with Glutathione-S-Transferase

Two cDNA clones representing fragments of the sequence encoding the GP28.5 protein were subcloned into the plasmid pGEX-2T [SMITH et al. Gene, 67, 31-40 (1988)]. The first clone, FM16, encodes the fifty-nine C-terminal amino acids of GP28.5, and the second clone, L, represents 212 amino acids of GP28.5.

Figure 3:
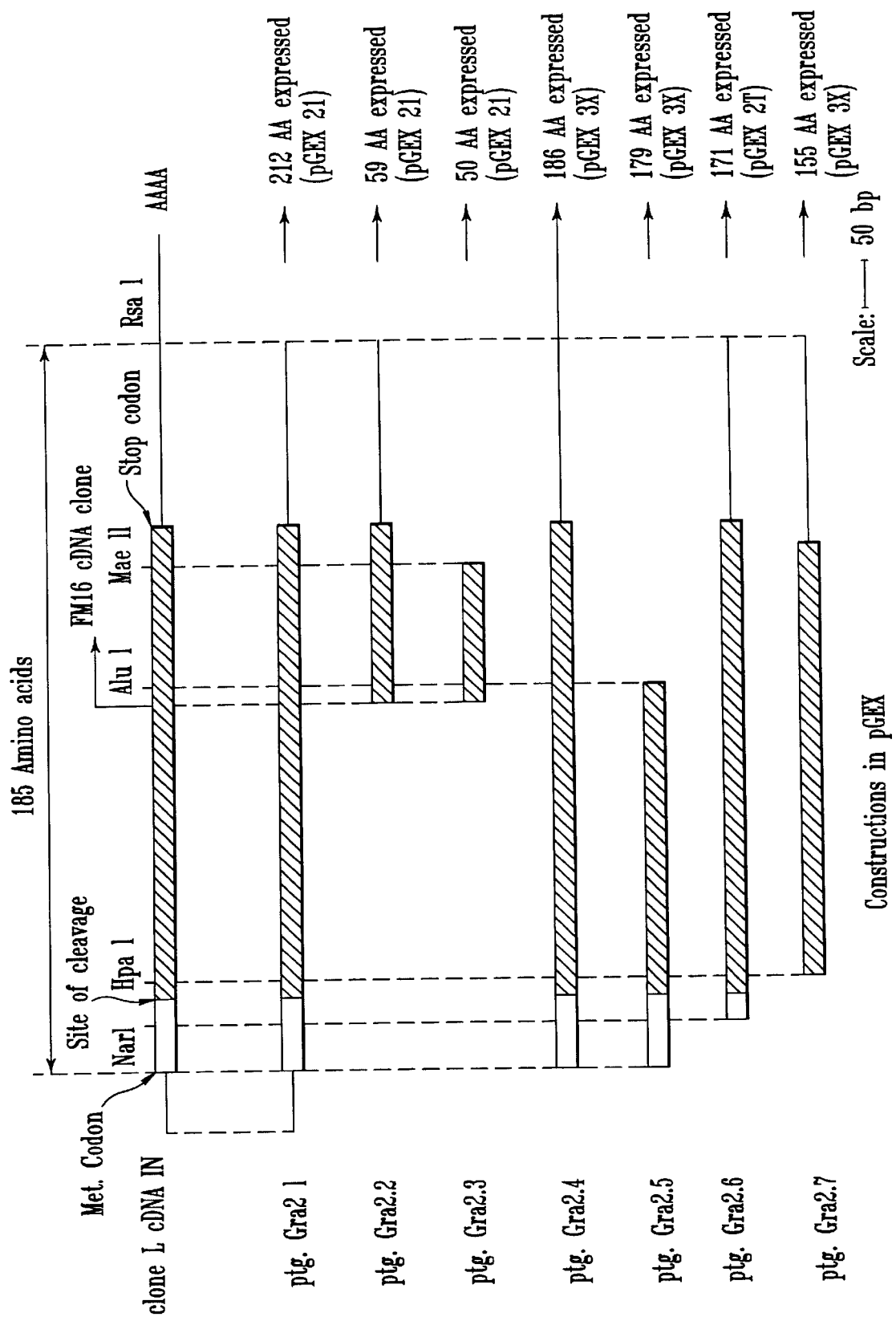
FIG. 3: Preparation of recombinant proteins comprising fragments of the GP28.5 sequence and Glutathione-S-Transferease. The names of the clones are indicated on the left portion of the figure and the Gp28.5 amino acids expressed are indicated on the right portion of the FIGURE.

5 other fragments (FIG. 3) encoding portions of the GP28.5 protein were also subcloned into the plasmids pGEX-2T and pGEX-3X (SMITH et al., cited):

the first clone, ptg.Gra2.1, derived from the LcDNA clone, encodes 212 amino acids including the 185 of GP28.5;

the second clone, ptg.Gra2.2, derived from the cDNA clone FM16, encodes the 59 C-terminal amino acids of the GP28.5 protein;

the third clone, ptg.Gra2.3, encodes 50 amino acids (amino acid 127 to amino acid 176 inclusive, see FIG. 3);

the fourth clone, ptg.Gra2.4, encodes 186 amino acids;

the fifth clone, ptg.Gra2.5, encodes 129 amino acids (N-terminal part of the GP28.5 protein, up to amino acid 129 inclusive);

the sixth clone, ptg.Gra2.6, encodes 171 amino acids (from amino acid 15 inclusive);

the seventh clone, ptg.Gra2.7, encodes 155 amino acids (from amino acid 31 inclusive).

The plasmids pGEX-2T and pGEX-3X containing the DNA inserts were used to transform *E. coli* JM 109 bacteria. The expression and purification of the recombinant proteins as well as of GST alone were carried out according to the procedure described by SMITH and JOHNSON (reference previously cited). A culture of *E. coli* JM 109 in the middle of the logarithmic phase was stimulated with 0.1 mM of IPTG. After growing for 1 hour at 37°, the cells were cooled on ice and centrifuged at 4000 rpm for 15 minutes. The pellet is resuspended in 0.02 M PBS, 0.5 mM PMSF, 1 mM EDTA, 1% TRITON X-100. The cells are sonicated on ice and centrifuged at 10,000 g for 5 minutes. The recombinant proteins are purified from the supernatant, by affinity chromatography on agarose-glutathione. The expression of the recombinant proteins was monitored by immunotransfer using the monoclonal antibody TG17-179 or mouse polyclonal serum directed against the purified GP28.5 antigen. The recombinant proteins corresponding to the clones ptg-.Gra2.2 (59 amino acids) and ptg.Gra2.3 (50 amino acids) were purified with a high yield. On the other hand, the recombinant proteins corresponding to the clones ptg.Gra2.1 (212 amino acids), ptg.Gra2.4 (186 amino acids) and ptg-.Gra2.5 (129 amino acids) were obtained with only low yields which appear to be due to the degradation of the proteins on the one hand, and on the other, to the presence of the signal sequence (the first 23 amino acids of the GP28.5 protein) in the recombinant proteins.

2) Fusion proteins with β-galactosidase

Recombinant lysogenic phages were produced from the original λgt11 clone FM16, in *E. coli* Y1089, according to the process described by HUYNH et al. [Glover, D.M. ed. vol. 1, 49–78 IRL Press, Oxford (1985)]. Crude lysates containing wild-type β-galactosidase or alternatively fusion protein [GP28.5/β-galactosidase] were prepared by inducing cultures at the logarithmic phase, by heating at 45° C. for 20 minutes and adding isopropyl-β-D-thiogalacto-pyranoside at a concentration of 10 mM. After additional incubation at 37° C. for 1 hour, the culture was concentrated, in a 0.01 M Tris buffer, pH8, 0.1 M EDTA, 10 mM NaCl, and then lysed by the addition of 0.25 mg of lysozyme, 0.01 M $MgCl_2$, and 0.2% TRITON X-100, and finally treated with DNAseI at 37° C. for 30 minutes.

The FM1 and FM16 clones react much more strongly with the TG17-179 antibody than the FM3 clone. The restriction map shows that the EcoRI inserts of 450 bp (FM3), 550 bp (FM1) and 650 bp (FM16) contain sequences which overlap.

The sequencing of these clones revealed that the reading frames in phase with that for β-galactosidase were only 17 bp for FM3, and 95 bp and 172 bp for FM1 and FM16 respectively, the rest of the inserts corresponding to the nontranslated 3' region plus the polyA tail. It therefore seems that the peptide corresponding to the 5 C-terminal amino acids of the GP28.5 antigen encoded by the FM3 clone is sufficient to obtain an antigenic reaction.

II) PURIFICATION OF THE GP28.5 ANTIGEN

EXAMPLE 3

Purification of the GP28.5 Antigen by HPLC $10^{10}$ tachyzoites of the RH strain were washed twice with 10 mM PBS, pH 7.2. After centrifugation at 1000 g for 10 minutes, the pellet was incubated overnight at 4° C. with gentle stirring, at a concentration of $10^9$ parasites/ml in TEN buffer (10 mM TRIS-HCl, pH 7.4; 2 mM EDTA; 150 mM NaCl) supplemented with 1% NONIDET P40, 100 U/ml of aprotinin and 40 μM PMSF. After centrifugation at 3500 g for 20 minutes, the supernatant was recovered and filtered on a 0.22 μm MILLIPORE membrane. The tachyzoite proteins extracted with NP40 were purified by reversed-phase HPLC chromatography in a C18 VYDAC column (300 Å, particle size: 7 μm, column dimensions: 500×9mm). 8 ml of crude protein extract were loaded onto the C18 column at 0% of solvent B [solvent A consists of 0.5% v/v of TFA in water; solvent B is a 25/75/0.45 (v/v) mixture of water/acetonitrile/TFA]. After 10 minutes of isocratic elution, the proteins are eluted with a 0 to 100% gradient of solvent B, for a period of 180 minutes, at an elution rate of 2 ml per minute, and detected at 215 nanometers. In order to locate the GP28.5 antigen, each HPLC fraction was freeze-dried, and the freeze-dried product was diluted in 100 μl of a TEN/PBS mixture [10 mM, pH 8 (v/v)]. 1 μl of each fraction was tested by dot-blot using the monoclonal antibody TG17-179. 10 μl (which corresponds to about 12 μg of purified protein) of each of the fractions which showed a positive reaction were loaded on an acrylamide gel in the presence of 2-ME. A silver nitrate staining of the gel made it possible to check their homogeneity and their purity. A similar gel was prepared and used for the electrophoretic transfer onto nitrocellulose membrane. The antigenicity of the fractions was evaluated by incubating the membrane with the monoclonal antibody TG17-179. The detection was performed with peroxidase-labeled antimouse IgG antibodies.

The major component of the eluate is the GP28.5 protein. The only contaminant detected is a 65 kDa protein which is also recognized by the TG17-179 antibody, and which may therefore represent either a dimer of GP28.5, or a related antigen.

II) IMMUNOLOGICAL PROPERTIES OF THE GP28.5 ANTIGEN AND ITS FRAGMENTS

EXAMPLE 4

Immunization of Mice and Protection Trials 8 to 10-week old female OF1 mice were immunized in the following manner: forty-two, thirty-five, twenty-seven and seven days before the infection, the following antigens:

ESA corresponding to the secretion of $5 \times 10^7$ tachyzoites; or alternatively, 15 µg of GP28.5 purified by HPLC as described in Example 3 were suspended in 100 µl of PBS, emulsified with 100 µl of incomplete FREUND's adjuvant and administered by subcutaneous injection.

Control mice were treated according to the same procedure with PBS supplemented with 100 µl of incomplete FREUND's adjuvant.

On the day of the infection, the sera were collected, then a suspension of 1200 cysts in 0.3 ml of PBS, pH 7.2, was administered orally.

The sera from mice immunized with ESA or GP28.5 purified by HPLC were tested by immunoelectrophoretic transfer, against tachyzoite ESA antigens extracted with NP40, in order to determine if they recognize the GP28.5 antigen.

It appears that the immunoreactivity profile is essentially the same whether the visualization is made with mouse immunoserum or with the monoclonal antibody TG17-179: in both cases, three bands of about 100, 65 and 28 kDa are visualized. The two bands with the highest molecular weight which are recognized by the TG17-179 antibody probably represent GP28.5 polymers.

Figure 2:
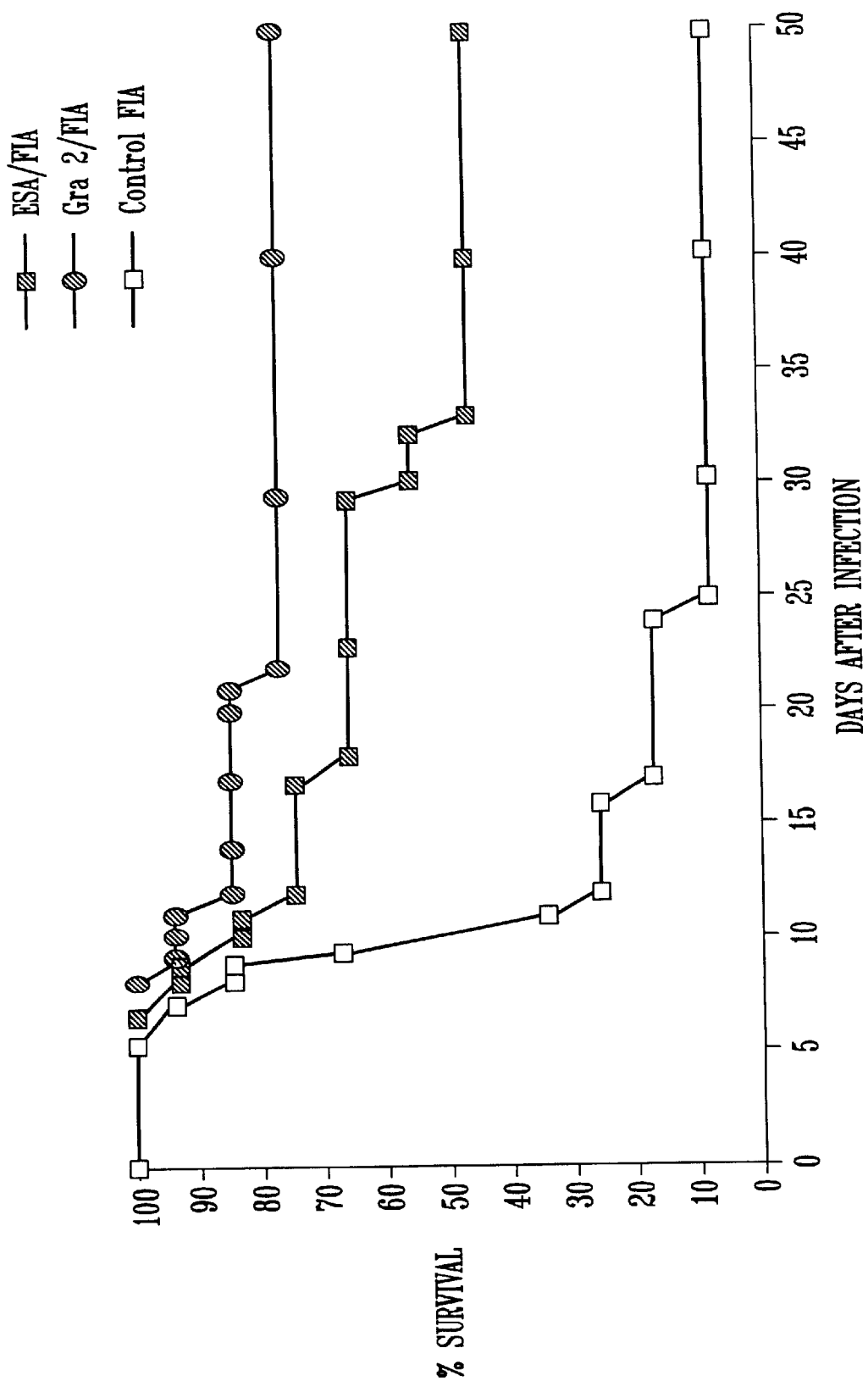
FIG. 2: The percentage of mice surviving after infection with *Toxoplasma gondii* immunized with ESA, Gra2 or PBS (control).

FIG. 2 represents the percentage of mice surviving after the infection. This figure shows that, whereas only 25% of the control mice immunized solely with incomplete FREUND's adjuvant survive 15 days after the infection, 75% of the mice immunized with the GP28.5 antigen purified by HPLC are still alive 50 days after the infection. When the mice are immunized with the ESA antigens, 45% survive 50 days after the infection. These results show that the immunization with the HPLC-purified GP28.5 antigen leads to a significant protection.

EXAMPLE 5

Reactivity of Human Sera with the Recombinant Proteins and Recognition of the C-terminal Epitope The human sera were obtained from patients carrying a chronic *Toxoplasma gondii* infection (TG positive). Sera from healthy patients were used as control (TG negative). The test was carried out by ELISA, and the visualization made using biotinylated anti-human IgG antibodies; the binding of these antibodies was detected using peroxidase-labeled streptavidin-biotin complexes. The peroxidase substrate used is OPD and the optical density was measured at 492 nm and expressed with respect to a control done using as antigen GST, according to the following formula: OD=OD of the serum reacting with the recombinant protein of 59 amino acids—OD of the serum reacting with GST. Under these conditions, the mean optical density of the TG-negative sera was 0.23. 74% of the fifty-nine TG-positive sera were above this optical density. The correlation with a conventional test of the anti-TG antibodies is: R=0.74 P.

In spite of this correlation, patients having 50 to 100 IU/ml of anti-TG IgG show very dispersed values for levels of antibodies against the FM16 recombinant protein (the optical densities range between 0.35 and 1.5). It therefore seems that a homogeneous level of anti-TG antibodies can in fact reflect varying responses to the GP28.5 antigen.

Ten sera which are negative by ELISA against the protein containing the fifty-nine amino acids were tested by immunotransfer against the fusion protein containing the 212 amino acids (LcDNA clone). Eight of these sera react with the protein comprising the 212 amino acids, whereas 7 of the control sera react negatively. It is probable that these 8 sera recognize epitopes present on the protein of 212 amino acids, and nearer the N-terminal end than those carried by the protein comprising the fifty-nine amino acids.

The binding of TG17-179 to the recombinant antigen FM16 was tested by competitive ELISA in the presence of sera from infected patients; the serum was added at a dilution of 1/100 to the solution of monoclonal antibodies.

These competition trials between TG17-179 and sera from infected patients show that the human polyclonal antibodies react with the C-terminal epitope of GP28.5: among the 12 human sera tested, 10 inhibit at varying degrees the binding of TG17-179 to the FM16 fusion protein.

The reactivity of the fusion proteins produced by the FM1 and FM3 clones with the TG17-179 antibody was also tested; FM1 and FM16 react much more strongly with the TG17-179 antibody than the FM3 clone.

Now, the sequencing of these clones has revealed that the reading frame in phase with that for β-galactosidase, is only 17 bp for FM3, and 95 bp and 172 bp for FM1 and FM16 respectively. It therefore appears that the peptide encoded by the FM3 clone, and corresponding to the 5 C-terminal amino acids of the GP28.5 antigen is sufficient in order to obtain an antigenic reaction.

However, since it also appeared that the binding of the monoclonal antibody TG17-179 to this FM3 peptide is weaker than the binding of said antibody to the peptides encoded by the longer clones FM1 and FM16, the inventors undertook to determine the optimal length of the epitope.

EXAMPLE 6

Immunoreactivity of Synthetic Peptides Corresponding to the C-terminal End of GP28.5

Peptides overlapping and covering the carboxy-terminal sequence of GP28.5 (1 to 15 residues) were synthesized, using the MERRIFIELD method.

They were tested by competitive ELISA with the FM16 fusion protein.

The fifteen terminal amino acids of GP28.5 contain the epitope reacting with the monoclonal antibody TG17-179. The capacity of this peptide to inhibit the reactivity in ELISA against the recombinant protein containing the fifty-nine amino acids, of sera obtained from patients suffering from acute or chronic infections was tested. Both types of sera (acute and chronic) are inhibited, to a varying degree, by the C-terminal peptide of fifteen amino acids. For the chronic sera, the percentage of inhibition varies from 8 to 100% and no correlation is observed with the starting optical density. The low level of inhibition observed for some sera may be due to the presence of antibodies with low affinity for this peptide. However, even on multiplying by ten the concentration of the peptide, the percentage inhibition is not increased. The specificity of the inhibition was demonstrated using as control a peptide with a different sequence and similar length. The percentage inhibition of the acute sera varies from 15 to 90% and is also independent of the starting optical density.

The inhibition studies carried out therefore show that the peptide of 15 amino acids comprises a major epitope of the C-terminal region of fifty-nine amino acids, for four out of twelve of the sera obtained from chronic patients, and for three out of twelve of the sera obtained from patients suffering from acute infections. In addition, three out of twelve of the chronic sera, and four out of twelve of the acute sera, show a partial inhibition (35–80% inhibition).

It therefore appears that the polyclonal response to the GP28.5 antigen involves a reactivity with the fifteen C-terminal amino acids, a reactivity of which the degree varies according to the individual. On the other hand, the degree of this response apparently does not vary between the acute infection and the chronic infection, no difference in the average percentage inhibition for each of the two groups having been observed.

However, five out of twelve chronic sera and five out of twelve acute sera which react with the C-terminal region of fifty-nine amino acids of GP28.5 do not react with the peptide of fifteen C-terminal amino acids, which shows that other major B epitopes exist in this region of fifty-nine amino acids and especially in the fragment corresponding to amino acids 127–176 of the sequence of the GP28.5 antigen.

In the case of C-terminal peptides having less than 15 amino acids, results are the following:

The strongest inhibition of the binding of the monoclonal antibody TG17-179 to the fusion protein is obtained with peptides comprising between 11 and 15 residues.

The inhibition is however obtained with the octapeptide comprising the 8 C-terminal residues.

The binding of TG17-179 to the C-terminal heptapeptide is 8 times weaker than its binding to the octapeptide. Finally, the immunoreactivity of the synthetic peptide is lost when it comprises 6 C-terminal amino acids or less.

The octapeptide lacking its COOH functional group and the octapeptide comprising two additional C-terminal residues (alanine) were also tested. These two peptides have practically the same activity as the C-terminal octapeptide: this shows that the carboxyl functional group is not necessary for the immunoreactivity of the epitope recognized by TG17-179.

The same peptides were tested by direct ELISA. Under these conditions, the immunoreactivity as a function of the length of the peptide decreases more rapidly: it is indeed lost for peptides of less than 10 residues in length. Consequently, it appears that by direct ELISA, the monoclonal antibody requires a longer peptide than in the inhibition test. In this particular case, it is unlikely that this is due to a poor absorption of the shortest peptides onto the microtiter plate, given the hydrophobic nature of the amino acids of said peptides.

Peptides lacking C-terminal residues were also synthesized: whereas the incubation of TG17-179 with the synthetic octapeptide covering the entire C-terminal residues inhibits the binding of the recombinant fusion protein, the corresponding heptapeptide lacking the carboxy-terminal glutamine residue is 64 times less active as competitor, and the hexapeptide lacking the two carboxy-terminal residues is 104 times less active.

We claim:

1. An isolated polypeptide, comprising at least one B cell epitope of Toxoplasma GP28.5 antigen, wherein the polypeptide is selected from the group consisting of
   (a) a polypeptide consisting of amino acids 170 to 185 of SEQ ID NO: 2,
   (b) a fragment of polypeptide (a), wherein the fragment consists of amino acids 180 to 185 of SEQ ID NO: 2, and
   wherein said GP28.5 antigen is a secreted antigen.

2. The polypeptide of claim 1, which is (a).

3. The polypeptide of claim 1, which is (b).

4. An anti-Toxoplasma vaccine, comprising the polypeptide of claim 1 and a pharmaceutically inert ingredient.

5. An immunogenic composition, comprising the polypeptide of claim 1 and a physiologically inert ingredient.

6. A process for preparing anti-GP28.5 antibodies, comprising:
   immunizing an animal with the immunogenic composition of claim 5, and
   recovering anti-GP28.5 antibodies from the animal.

7. A fusion polypeptide, comprising a fragment of Toxoplasma GP28.5 antigen comprising at least one epitope of the Toxoplasma GP28.5 antigen fused to a heterologous polypeptide sequence, wherein the fragment of the Toxoplasma GP28.5 antigen is selected from the group consisting of
   (a) a fragment consisting of amino acids 170 to 185 of SEQ ID NO: 2,
   (b) a fragment consisting of amino acids 180 to 185 of SEQ ID NO: 2, and
   wherein said GP28.5 antigen is a secreted antigen.

8. The fusion polypeptide of claim 7, wherein the fragment of the Toxoplasma GP28.5 antigen is (a).

9. The fusion polypeptide of claim 7, wherein the fragment of the Toxoplasma GP28.5 antigen is (b).

10. An anti-Toxoplasma vaccine, comprising the fusion polypeptide of claim 7, and a pharmaceutically inert ingredient.

11. An immunogenic composition, comprising the fusion polypeptide of claim 7, and a pharmaceutically inert ingredient.

12. A process for preparing GP28.5 antibodies, comprising:
   immunizing an animal with the immunogenic composition of claim 11, and
   recovering anti-GP28.5 antibodies from the animal.

* * * * *

UNITED STATES PATENT AND TRADEMARK OFFICE
CERTIFICATE OF CORRECTION

PATENT NO. : 6,392,014 B1
DATED : May 21, 2002
INVENTOR(S) : Cesbron et al.

It is certified that error appears in the above-identified patent and that said Letters Patent is hereby corrected as shown below:

<u>Title page,</u>
Item [76], Inventors, should read:

-- [76]  Inventors: Marie-France Cesbron, Marcq-en-Baroeul; Corinne Mercier, Sains du Nord; Andre Capron, Phalempin; André Tartar, Vitry en Artois; Pierrette Maes, Wasquehal, all of (FR) --

Signed and Sealed this

Third Day of June, 2003

JAMES E. ROGAN
*Director of the United States Patent and Trademark Office*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 2152 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: join(886..1035, 1275..1682)

(ix) FEATURE:
      (A) NAME/KEY: exon
      (B) LOCATION: 886..1035

(ix) FEATURE:
      (A) NAME/KEY: exon
      (B) LOCATION: 1275..1682

(ix) FEATURE:
      (A) NAME/KEY: intron (B) LOCATION: 1036..1274

(xi) SEQUENCE DESCRIPTION: SEQ ID NO:1:

```
CTGCAGTCTT AATCATTTCC ACATAGTTTT TGTTCCCCCA GACAATCAAT CCTGGCTGAG      60

CCCCCCATGT ACGCGTTACC ACCTGCCAGT GCATATGGGT TTGCATATTT TTGCTGAAGT     120

CCGAAAGAGG GGCCACGCAA AACGTTACCG GTTTGCTGCA GGCAGCCAGG TAGGTGGAAC     180

AGATCTCCAG CGAGTACGAC CACTGTGCGT GTACTTACGC CAAAAGGAAA ATACACCTGC     240

ACCGCTATTA GCGGCAGTC GTCTACCTGA ATCGTCTCCC CGGCCTCATC ATTTTGTTCG      300

ACACAAGTTT CCATTAGGAC TTTGTGACAG TCGTCTGCTC TCGACCTTCC AACCGTCTCG     360

TGGACGAAAA ATCCTCGGGT GACTTGCCGT GGACGAACGC CTCCCGTTTG CTTCTACAAG     420

TGACTATGCG ATAGGTTCCG CAGTGCAGCC AGGCTTGCGA AAAACAAGTT CGTCGCAAAA     480

GGTTAATTAC CTACGCACCA CGAAGGAAAA CGCGTATCAC GTCAGTCCTT ACGGTCAATA     540

TACAAATACT TGGCCGTCCA GTGGAGGCAA CGTGCCCGTC GCACGGTGAT ACTGACTGGT     600

GACTTGCACG TACGTCTCTC GCCGGCGTCC AAACCAAATT GACCCGGGGC AGCCTACTCC     660

CTGTCGTCCC TTAGGCTAAG TGCGAGCAAC ATCTCTACAC AGAGACGACG CCAGAGACGC     720

AAAATGAACA GCGGAACCTG CGTCGCTGTC TGTCCTGCGA ACTGATGACA GAAAGGGTCA     780

TTAAACGATT TCTTTTGCAA TTCGCGTCGT TATCGCACGT TGTTTCTCTT CCCACGAATA     840

GTTGTTTTGA TTAGATATTG CTTCTTCTCC ACATATCGCC TCACA ATG TTC GCC          894
                                                Met Phe Ala
                                                  1
```

```
GTA AAA CAT TGT TTG CTG GTT GTT GCC GTT GGC GCC CTG GTC AAC GTC       942
Val Lys His Cys Leu Leu Val Val Ala Val Gly Ala Leu Val Asn Val
      5                  10                  15

TCG GTG AGG GCT GCC GAG TTT TCC GGA GTT GTT AAC CAG GGA CCA GTC       990
Ser Val Arg Ala Ala Glu Phe Ser Gly Val Val Asn Gln Gly Pro Val
 20                  25                  30                  35

GAC GTG CCT TTC AGC GGT AAA CCT CTT GAT GAG AGA GCA GTT GGG          1035
Asp Val Pro Phe Ser Gly Lys Pro Leu Asp Glu Arg Ala Val Gly
                 40                  45                  50
```

```
TAAGTTGGCA AAAGTAATGA TAGAGGCAGG GGTTGAACGA TAGGCGGCTG CAGATTTGTA    1095

TAACACAACA TGATGTAGCT GCCACGGTTT TTTTTCGGAG AGTGATGCCG TCTGACTGTC    1155

ATCGCACCCA TGGGAGCTAG GGAGGTGCGC TTCTGTGTGA TATGTATTGT CCTAGTCCAA    1215

TTTCCCACGC ACTGTAGTGT CTTGAGACTC GGTGCCATGT AGAATTTTGT GTCTGCAGA    1274
```

```
GGA AAA GGT GAA CAT ACA CCA CCA CTC CCA GAC GAG AGG CAA CAA GAG     1322
Gly Lys Gly Glu His Thr Pro Pro Leu Pro Asp Glu Arg Gln Gln Glu
                     55                  60                  65

CCA GAA GAA CCG GTT TCC CAA CGT GCA TCC AGA GTG GCA GAA CAA CTG     1370
Pro Glu Glu Pro Val Ser Gln Arg Ala Ser Arg Val Ala Glu Gln Leu
             70                  75                  80

TTT CGC AAG TTC TTG AAG TTC GCT GAA AAC GTC GGA CAT CAC AGT GAG     1418
Phe Arg Lys Phe Leu Lys Phe Ala Glu Asn Val Gly His His Ser Glu
         85                  90                  95

AAG GCC TTC AAA AAA GCA AAG GTG GTG GCA GAA AAA GGC TTC ACC GCG     1466
Lys Ala Phe Lys Lys Ala Lys Val Val Ala Glu Lys Gly Phe Thr Ala
     100                 105                 110

GCA AAA ACG CAC ACG GTT AGG GGT TTC AAG GTG GCC AAA GAA GCA GCT     1514
Ala Lys Thr His Thr Val Arg Gly Phe Lys Val Ala Lys Glu Ala Ala
115                 120                 125                 130

GGA AGG GGC ATG GTG ACC GTT GGC AAG AAA CTC GCG AAT GTG GAG AGT     1562
Gly Arg Gly Met Val Thr Val Gly Lys Lys Leu Ala Asn Val Glu Ser
                 135                 140                 145
```

-continued

```
GAC AGA AGC ACT ACG ACA ACG CAG GCC CCC GAC AGC CCT AAT GGC CTG        1610
Asp Arg Ser Thr Thr Thr Thr Gln Ala Pro Asp Ser Pro Asn Gly Leu
            150                 155                 160

GCA GAA ACC GAG GTT CCA GTG GAG CCC CAA CAG CGG GCC GCA CAC GTG        1658
Ala Glu Thr Glu Val Pro Val Glu Pro Gln Gln Arg Ala Ala His Val
            165                 170                 175

CCC GTC CCA GAC TTT TCG CAG TAA TGTTGACTAC GACGAAAGTG ATGCGCAGGC       1712
Pro Val Pro Asp Phe Ser Gln  *
            180             185

TGGAAAGCCG CTGAAGGGAG AAGTCTACAA AGCCGATCAG TGAAAAATGT GTGGGGAGGT     1772

GGTCTTGTTG CAGGAATGCA ATGTGTTAAG CATCGTGTTC GAATGCAGTG CGTGTATCAG     1832

TTGTGCGCGG AAGGACACTG CTTCAATGTT AAGAACCTGT TTTCTCCGTA GAGAGGACCA     1892

AAAGACGATT GCAAAACTGG TATGTACGCA ATAGCCCAAT GCCGGACGTC AGTTGGTTGT     1952

ATGTGACGCT CCCAGATGTC ATATGCCTTG TGAGTGTGTC TGGGATGCAA GTTTTTGGTG     2012

TGCGTTGATT TCGCCAGCTT ATGACAGTGG CAGACGAATT ATTGACATGA TACAAGGACG     2072

CAGAAAGGAA CAAACACCGT AGTTCCAGTC GACACAGAAA GGGAGGGTAA AGAAAGTAAT     2132

TGAAAGGTGA TTTTAGATAA                                                 2152
```

(2) INFORMATION FOR SEQ ID NO:2:

(i) SEQUENCE CHARACTERISTICS:
        (A) LENGTH: 185 amino acids
        (B) TYPE: amino acid
        (D) TOPOLOGY: linear (ii) MOLECULE TYPE: protein (xi) SEQUENCE DESCRIPTION: SEQ ID NO:2:

```
Met Phe Ala Val Lys His Cys Leu Leu Val Val Ala Val Gly Ala Leu
 1               5                  10                  15

Val Asn Val Ser Val Arg Ala Ala Glu Phe Ser Gly Val Val Asn Gln
                20                  25                  30

Gly Pro Val Asp Val Pro Phe Ser Gly Lys Pro Leu Asp Glu Arg Ala
            35                  40                  45

Val Gly Gly Lys Gly Glu His Thr Pro Pro Leu Pro Asp Glu Arg Gln
 50                  55                  60

Gln Glu Pro Glu Glu Pro Val Ser Gln Arg Ala Ser Arg Val Ala Glu
 65                  70                  75                  80

Gln Leu Phe Arg Lys Phe Leu Lys Phe Ala Glu Asn Val Gly His His
                85                  90                  95

Ser Glu Lys Ala Phe Lys Lys Ala Lys Val Val Ala Glu Lys Gly Phe
                100                 105                 110

Thr Ala Ala Lys Thr His Thr Val Arg Gly Phe Lys Val Ala Lys Glu
            115                 120                 125

Ala Ala Gly Arg Gly Met Val Thr Val Gly Lys Lys Leu Ala Asn Val
 130                 135                 140

Glu Ser Asp Arg Ser Thr Thr Thr Gln Ala Pro Asp Ser Pro Asn
145                 150                 155                 160

Gly Leu Ala Glu Thr Glu Val Pro Val Glu Pro Gln Gln Arg Ala Ala
                165                 170                 175

His Val Pro Val Pro Asp Phe Ser Gln
            180                 185
```